United States Patent
Kappler

(10) Patent No.: US 9,075,153 B2
(45) Date of Patent: Jul. 7, 2015

(54) METHOD FOR CORRECTING COUNT RATE DRIFT IN A QUANTUM-COUNTING DETECTOR, AN X-RAY SYSTEM WITH A QUANTUM-COUNTING DETECTOR AND A CIRCUIT ARRANGEMENT FOR A QUANTUM-COUNTING DETECTOR

(75) Inventor: Steffen Kappler, Effeltrich (DE)

(73) Assignee: SIEMENS AKTIENGSELLSCHAFT, Munich (DE)

( * ) Notice: Subject to any disclaimer, the term of this patent is extended or adjusted under 35 U.S.C. 154(b) by 446 days.

(21) Appl. No.: 13/483,326

(22) Filed: May 30, 2012

(65) Prior Publication Data

US 2012/0305757 A1    Dec. 6, 2012

(30) Foreign Application Priority Data

May 31, 2011    (DE) .......................... 10 2011 076 781

(51) Int. Cl.
  *G01T 1/40*    (2006.01)
  *A61B 6/03*    (2006.01)

(52) U.S. Cl.
  CPC . *G01T 1/40* (2013.01); *A61B 6/037* (2013.01); *A61B 6/032* (2013.01)

(58) Field of Classification Search
  CPC ........... G01T 1/40; A61B 6/032; A61B 6/037
  See application file for complete search history.

(56) References Cited

U.S. PATENT DOCUMENTS

| | | | |
|---|---|---|---|
| 7,208,739 B1 | 4/2007 | Wen | |
| 2005/0123090 A1 | 6/2005 | Heismann et al. | |
| 2006/0146984 A1* | 7/2006 | Bruder et al. | 378/9 |
| 2009/0039273 A1* | 2/2009 | Tkaczyk et al. | 250/370.06 |
| 2010/0193700 A1 | 8/2010 | Herrmann et al. | |
| 2010/0270472 A1 | 10/2010 | Proksa et al. | |
| 2011/0051901 A1 | 3/2011 | Michel et al. | |
| 2012/0037810 A1 | 2/2012 | Scott et al. | |
| 2013/0334433 A1* | 12/2013 | Spartiotis et al. | 250/370.09 |

FOREIGN PATENT DOCUMENTS

| | | |
|---|---|---|
| CN | 101680956 A | 3/2010 |
| DE | 10357187 A1 | 6/2005 |
| DE | 102006006411 A1 | 8/2007 |
| JP | 11142521 A | 5/1999 |
| WO | WO 2008146218 A2 | 12/2008 |
| WO | WO 2010133871 A2 | 11/2010 |

OTHER PUBLICATIONS

Chinese Office Action and English translation thereof dated Mar. 7, 2014.
German Priority Document DE 10 2011 076 781.9 filed May 31, 2011 (not yet published).

* cited by examiner

*Primary Examiner* — Yara B Green
(74) *Attorney, Agent, or Firm* — Harness, Dickey & Pierce, P.L.C.

(57) ABSTRACT

A method, a circuit arrangement and an X-ray system, in particular a CT system, are disclosed wherein, in order to correct the count rate drift of a detector for ionizing radiation having quantum-counting detector elements which include a combination of at least two counters with significantly different energy thresholds, and on the basis of previously determined functional dependencies of count rates on one another and using at least one of the counters per detector element as the reference, the count rates of the respective other counters with different energy thresholds are corrected.

15 Claims, 3 Drawing Sheets

METHOD FOR CORRECTING COUNT RATE DRIFT IN A QUANTUM-COUNTING DETECTOR, AN X-RAY SYSTEM WITH A QUANTUM-COUNTING DETECTOR AND A CIRCUIT ARRANGEMENT FOR A QUANTUM-COUNTING DETECTOR

PRIORITY STATEMENT

The present application hereby claims priority under 35 U.S.C. §119 to German patent application number DE 10 2011 076 781.9 filed May 31, 2011, the entire contents of which are hereby incorporated herein by reference.

FIELD

At least one embodiment of the invention generally relates to a method for correcting count rate drift in a detector of an X-ray system, particularly a CT system, having quantum-counting detector elements, each detector element comprising a combination of at least two counters with significantly different energy thresholds which are evaluated in combination in order to determine an incident radiation dose. At least one embodiment of the invention also generally relates to an X-ray system with a quantum-counting detector and/or a circuit arrangement for a quantum-counting detector.

BACKGROUND

X-ray systems, particularly CT systems with quantum-counting detectors, and methods for evaluating the detector pulses originating from the detectors are generally known. More recently, as distinct from the previously used conventional detector types with integrating detector elements, quantum-counting detectors of the type in question have been proposed for use in CT systems because they offer a possible solution to the problem of reducing the patient dose and of energy-resolving measurement in single-source CT systems. In the case of such quantum-counting detectors, the high X-ray photon fluxes lead, in clinical CT scanners, to the build-up of space charges in the CdTe/CdZnTe detector—materials that are typically used, which can result in significant count rate drift. This count rate drift makes precise dose determination more difficult and leads, in general, to imaging errors and, particularly severely in CT systems, to artifacts in the tomographic images created from absorption data.

SUMMARY

In at least one embodiment of the invention, a method is provided for correcting count rate drift in quantum-counting detectors and an improved X-ray system with a quantum-counting detector.

Advantageous developments of the invention are the subject matter of the subclaims.

Taking account of this knowledge, the inventor proposes, in at least one embodiment, a method for correcting count rate drift for a detector of ionizing radiation having a plurality of quantum-counting detector elements arranged over an area, each detector element comprising a combination of at least two counters with significantly different energy thresholds that are evaluated in combination to determine an incident radiation dose. According to at least one embodiment of the invention, based on previously determined functional dependencies of count rates on one another and using at least one of the counters per detector element as a reference, the count rates of the respective other counters with a different energy threshold are corrected.

In addition to at least one embodiment of the inventive method, the inventor also proposes an X-ray system, in particular a CT system, having a detector with quantum-counting detector elements, a combination of at least two counters with significantly different energy thresholds being associated with each detector element, and a control and computer unit which comprises a program memory in which computer programs are stored and which, during operation, carries out at least one embodiment of the inventive method.

BRIEF DESCRIPTION OF THE DRAWINGS

The invention will now be described in greater detail making reference to the preferred example embodiments and with the aid of the drawings, wherein only the features necessary for understanding the invention will be described. The following reference signs are used: 1: CT system; 2: first beam source; 3: first detector; 4: second beam source; 5: second detector; 6: gantry housing; 7: patient; 8: patient support; 9: system axis; 10: computer station; D: detector; Dn,m: detector elements; I1, I2, I3: pulse rates/count rates; L/K: Logic and correction unit; Lcorr: pulse rate; Prg1-Prgn: computer programs; S1, S2, S3: threshold value; ZS1, ZS2, ZS3: counters.

In the drawings.

Figure 1:
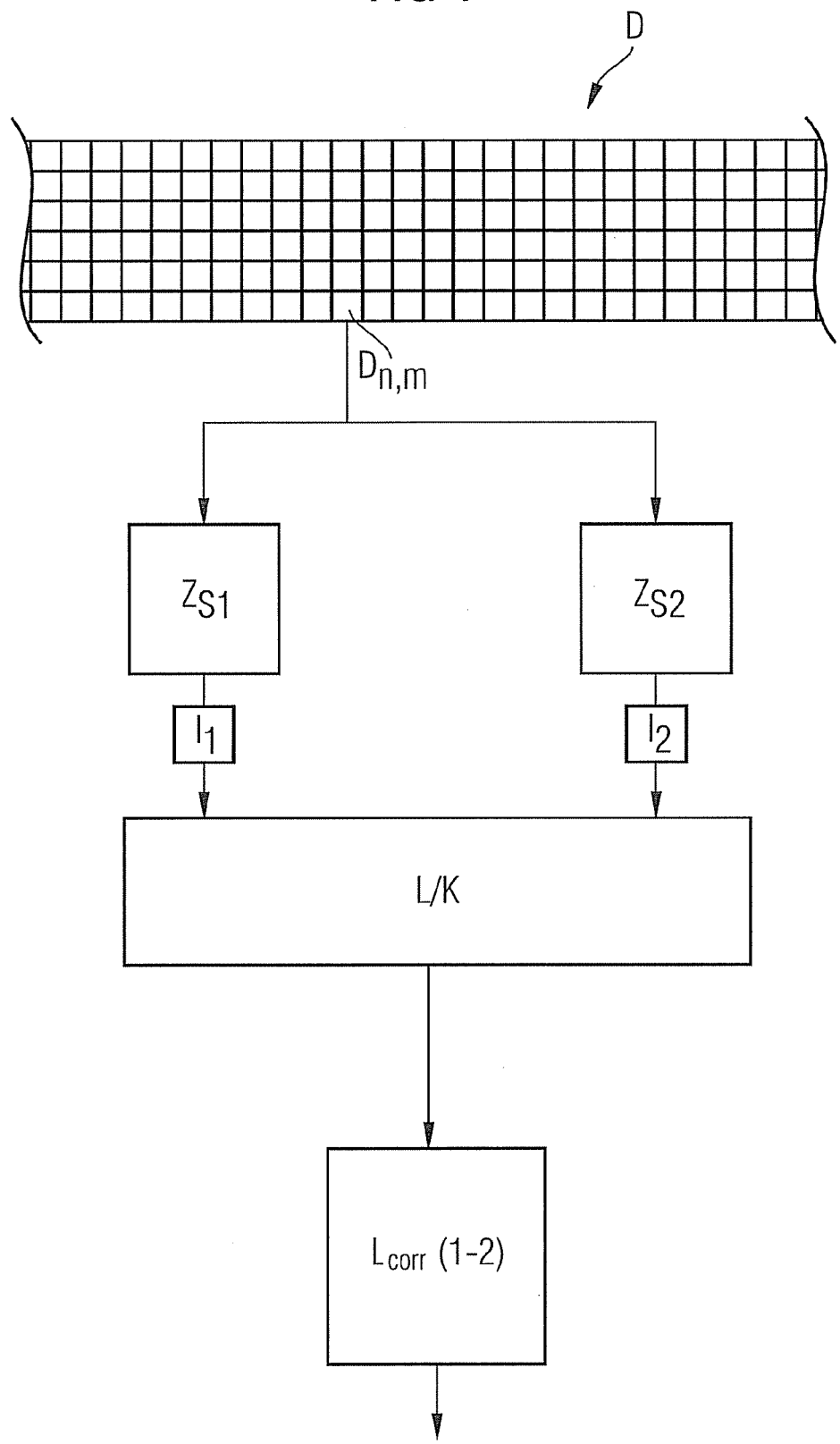
FIG. 1: is a schematic representation of a detector electronic system of a detector element comprising two counters.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with the conventional design of quantum-counting detectors, for the purpose of signal measurement at a detector material, at least two different energy thresholds are used which are equivalent to the incident energy of a particle in the detector material, the exceeding of said thresholds being counted in each case. The inventor has observed that an astonishing constancy exists in the ratio of count rates of significantly different energy thresholds—for example 20 keV and 60 keV or 20 keV, 35 keV and 60 keV for the measurement of a scan with a 120 kVp spectrum—to one another. This is the case for most polychromatic X-ray spectra that are typically used in X-ray diagnostics, in combination with the detector pixel sizes that are commonplace therein.

It will be shown in the following description of embodiments of the method how this property can be used for eliminating count rate drift and an improvement in image quality can be thereby achieved, even though at the cost of severely reduced spectral sensitivity. The constant factors which describe the ratios between the count rates of the counters to different threshold valves can be calculated as follows.

The count rate measured by the counter i is found from:

$$I_i = A_i \cdot I \cdot (1 - d_i), \quad (1)$$

where Ii is the radiation intensity emitted onto a detector element, Ai is the efficiency of the detector in combination with the counter i and di is the count rate drift of the counter i.

In the case where the drift values di are linked to one another in linear manner, this can be described as follows:

$$I_i = A_i \cdot I \cdot (1 - f_i \cdot d). \quad (2)$$

A change of the linear absorption scale into a logarithmic absorption scale or, more precisely, attenuation scale gives:

$$L_i = L - \ln(A_i) - \ln(1 - f_i \cdot d). \quad (3)$$

With the definition of $a_i := -\ln(A_i)$ and the use of the approximation $\ln(1+\chi) \approx \chi$ the following is obtained $$L_i = L + a_i + f_i \cdot d. \quad (4)$$

These equations enable access to the measurement of the count rate drift in each counter pair (i, j) of the measured data sets $$d = d_{ij} := \frac{(L_j - a_j) - (L_i - a_i)}{f_j - f_i}, \quad (5)$$

where precise knowledge of the parameters ai and fi is assumed.

The measured drift values can now be used in order to correct the measurement data and to extract the value L. We use the data measured with the counter k and the drift found from the counters i and j:

$$L = L_{k,ij} := L_k - a_k - f_k \cdot d_{ij}. \quad (6)$$

In the case k≡i or k≡j, the same relation can be expressed as $$L = L_{ij} := \frac{f_j}{f_j - f_i} \cdot (L_i - a_i) - \frac{f_j}{f_j - f_i}(L_j - a_j) \quad (7)$$

$$= w_{ij} \cdot (L_i - a_i) + (1 - w_{ij}) \cdot (L_j - a_j) \quad (8)$$

$$w_{ij} := \frac{f_j}{f_j - f_i} \quad (9)$$

which amounts to weighted addition of each pair (i, j) of measured data sets on a logarithmic scale. The mixed weighting wij is given by the count rate drift ratios fi and fj. It should be noted therein that ai and fi depend on the form of the pulse spectrum provided by the CdTe detector. Thus the drift ratios are subject to certain variations on a change in the X-ray spectrum, the absorption material and the thickness thereof based on the beam hardening which occurs. Pulse pile-up during a high X-ray photon flux also has an effect on these parameters.

The method described above requires precise calibration of the parameters ai and fi. Both parameters are sensitive to the form of the pulse spectrum and are therefore dependent on the following conditions:

Pulse characteristic of the detector, dependent on the detector material, geometry, bias voltage and signal shaping characteristics;

Spectrum of the incident radiation, dependent on the tube voltage (kV), filtration and beam hardening;

Pulse pile-up, dependent on the tube current (mA) and attenuation by the scanned material;

Threshold value of the counters used.

The procedure according to an embodiment of the invention will now be described for a given combination of tube voltage and tube current.

Due to the imprecise nature of the actual counter threshold and/or the variation of the effective pulse duration, calibration must be carried out channel by channel. For this purpose, we observe a quantum-counting detector with N≥2 counters, preferably N=2 or N=3 at significantly different threshold values. The counter with the lowest energy threshold is i=1 with the values, according to the definition, of a1=0 and f1=1. The measurements are carried out repeatedly for different attenuation values S=0 ... Ŝ.

In the context of medical imaging, it is useful to use a thickness d of water or water-equivalent material such that a realistic beam hardening results. This can be achieved with the use of a bar-pattern phantom having various thicknesses.

The following applies:

$$S(d) = \mu_{H_2O} \cdot d \quad (10)$$

For a given kV/mA combination, therefore, each bar of the phantom is scanned, including the case d=0. It is important that the detector shows a significant change in the count rate drift, and this can possibly be brought about by modification of the bias voltage during calibration. This scan can take place in the region of a few seconds to several seconds, depending on the quantum statistics necessary for carrying out the steps set out below.

The count rate data Ii from these scans is processed according to the following equations:

$$D_i(S) := -\ln I_i(S) - \ln \bar{I}_1(0) - S \quad (11)$$

$$\equiv a_i(S) + d_i(S) = a_i(S) + f_i(S) d_1(S), \quad (12)$$

where $\bar{I}_1(0)$ is the mean of $I_1$ over time without attenuation (S=0). This represents a "flat field correction". With the help of the calculation of a linear regression in a scatter diagram Di generated with this data against D1, the parameters ai(S) and fi(S) are found, ai(S) being the ordinate value at the intersection of the regression line with the ordinate and fi(S) being the gradient of the regression line.

The following relation therefore applies $$D_i(S) = a_i(S) + f_i(S) \cdot D_1(S). \quad (13)$$

In the subsequent step, the parameters al(S) and fl(S) can be modeled, for example by polynomial regression, in order to cover continuous attenuation values S. These values can be used to calculate and correct the count rate drift, as set out in equations (5) to (9).

It should be noted that, in the first processing step, the data Ii or Li should be subjected to a flat field correction to $\bar{I}_1(0)$. It should also be noted that the above method inherently includes a beam hardening correction and a saturation correction of the count rate.

An embodiment of the present method therefore uses the constancy of the ratios of the count rate drift values from counters with significantly different threshold values in order to correct the count rate drift. This correction can be applied at the level of the projection data and enables rapid and simple processing steps, in the context of both spiral scans and sequential scans. In contrast to other algorithms for ring artifact removal, this method does not influence the image sharpness, nor does it remove low-contrast objects.

An embodiment of the method described above assumes at least N=2 counters with significantly different threshold values for correcting $(N^2-N)/2$ data sets. Essentially all data sets from N counters are corrected for count rate drift. However, this correction is only precise if the material causing absorption during the scan is identical or at least similar to the material used for calibration. It is, however, error-prone for other materials, leading to a severely reduced multi-energy capability. However, it is possible, according to the formulae (7)-(9) to make available a number of $(N^2-N)/2$ material-related data sets which are free from count rate drift in relation to the respective reference material. Said material-related data sets have a spectral sensitivity and modified noise characteristic. Contrast levels from substances other than water will appear in accordance with the equation $C_{ij} = w_{ij} \cdot C_i + (1-w_{ij}) \cdot C_j$.

In the case of iodine-based contrast media, an advantageous accidental occurrence takes place during imaging: the mixed weighting for both the desired counters at approximately 20-30 keV and 60-70 keV is close to the mixed weighting that is required for maximizing the water-iodine contrast-to-noise ratio (CNR). This is found, for example, for the factors f12≈8 and w12≈1.14. Such image contrast values are similar to the measured values with 20 keV counters, in which case the image noise becomes slightly increased.

An embodiment of the present method could enable the use of CdTe or CdZnTe sensor materials with sub-optimal drift properties in clinical CT scanners and provide good image reproduction properties at the cost of severely reduced spectral sensitivity. However, this deficit can be compensated for by the use of a dual kVp method, for example in a dual source CT scanner.

Furthermore, it should be noted that it is essentially sufficient to determine the constant count rate ratios, that is, the above-mentioned factors fxy, between the counters x and y with different energy thresholds without empirical exactness, but to estimate said ratios roughly. The image artifacts which then remain can be processed with known algorithms, e.g. ring artifact removal algorithms, in the case of CT.

Taking account of this knowledge, the inventor proposes, in at least one embodiment, a method for correcting count rate drift for a detector of ionizing radiation having a plurality of quantum-counting detector elements arranged over an area, each detector element comprising a combination of at least two counters with significantly different energy thresholds that are evaluated in combination to determine an incident radiation dose. According to at least one embodiment of the invention, based on previously determined functional dependencies of count rates on one another and using at least one of the counters per detector element as a reference, the count rates of the respective other counters with a different energy threshold are corrected.

In order to prepare scans of particular materials, the functional dependencies of the count rates of the individual counters of each detector element can advantageously be measured under irradiation of the identical or, with regard to the absorption properties thereof, equivalent material of different thickness which will also be present in a later X-ray investigation in the measurement object that is to be investigated.

Furthermore, in order to determine the functional dependencies of the count rate drift of the detector elements of the detector, the coefficients of a linear regression can be determined between at least two counters and said coefficients can be used to correct the count rate of at least one of the counters.

As an alternative to observing purely linear dependencies, in order to determine the functional dependencies of the count rate drift of the detector elements of the detector, the coefficients of a polynomial regression can be determined between at least two counters and thus the count rate of at least one counter can be corrected.

Finally, it is particularly favorable if the measured count rates Ii and/or the logarithmic equivalent Li thereof are subjected to normalization, in particular a flat field correction, before use thereof.

In addition to at least one embodiment of the inventive method, the inventor also proposes an X-ray system, in particular a CT system, having a detector with quantum-counting detector elements, a combination of at least two counters with significantly different energy thresholds being associated with each detector element, and a control and computer unit which comprises a program memory in which computer programs are stored and which, during operation, carries out at least one embodiment of the inventive method.

FIG. 1 shows a schematic representation of a portion of a detector D with the detector electronics of a quantum-counting detector element Dn,m shown in rudimentary manner. In the detector electronics of the detector elements, the electrical signals are fed in parallel from the detector element Dn,m to two counters ZS1 and ZS2, the counters being set, according to their index, with different threshold values S1 and S2, for example 20 keV and 60 keV, so that only electrical signals which correspond to a gamma quantum of at least 20 keV or at least 60 keV incident in the detector element are counted. The counted pulse rates I1 and I2 are transferred by the counters ZS1 and ZS2 to a logic and correction unit L/K, in which the inventive drift correction of the measured count rates is carried out on the basis of the relation found between the count rates I1 and I2, and is output as a corrected logarithmic pulse rate Lcorr(1-2).

Figure 2:
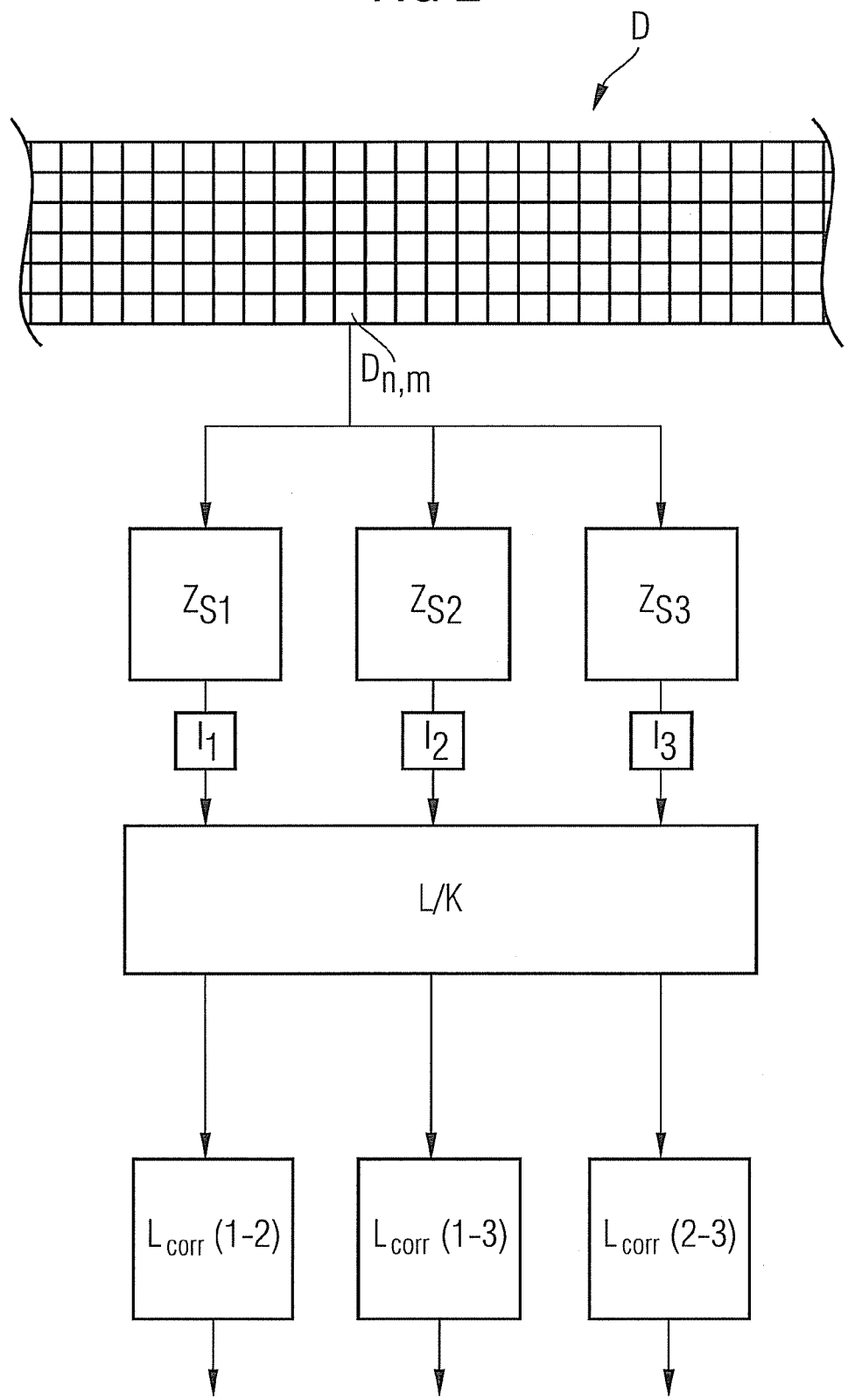
FIG. 2: is a schematic representation of a detector electronic system of a detector element comprising three counters.

A variant of an inventive detector with three counters per detector element is shown in FIG. 2. This figure again shows a schematic representation of a portion of a detector D with the detector electronics of a quantum-counting detector element Dn,m shown in rudimentary manner. In the detector electronics of the detector elements, the electrical signals are fed in parallel from the detector element Dn,m to three counters ZS1 to ZS3, the counters being set, according to their index, with different threshold values S1 to S3, for example 20 keV, 35 keV and 60 keV, so that in each counter, only electrical signals which correspond to the energy equivalent of a gamma quantum of at least 20 keV, 35 keV or at least 60 keV incident in the detector element are counted. The pulse rates I1 to I3 counted by the counters ZS1 to ZS3 are transferred to the logic and correction unit L/K, in which the inventive drift correction of the measured pulse rates I1 to I3 is corrected in each case, based on the relation found between the pulse rates, I1 with I2, I1 with I3 and I2 with I3 and is output as a corrected logarithmic pulse rate Lcorr(1-2), Lcorr(1-3) and Lcorr(2-3). Alternatively, a single corrected logarithmic pulse rate can be output, wherein a single corrected calculated value, for example a mean value, is determined from the corrected individual values.

Figure 3:
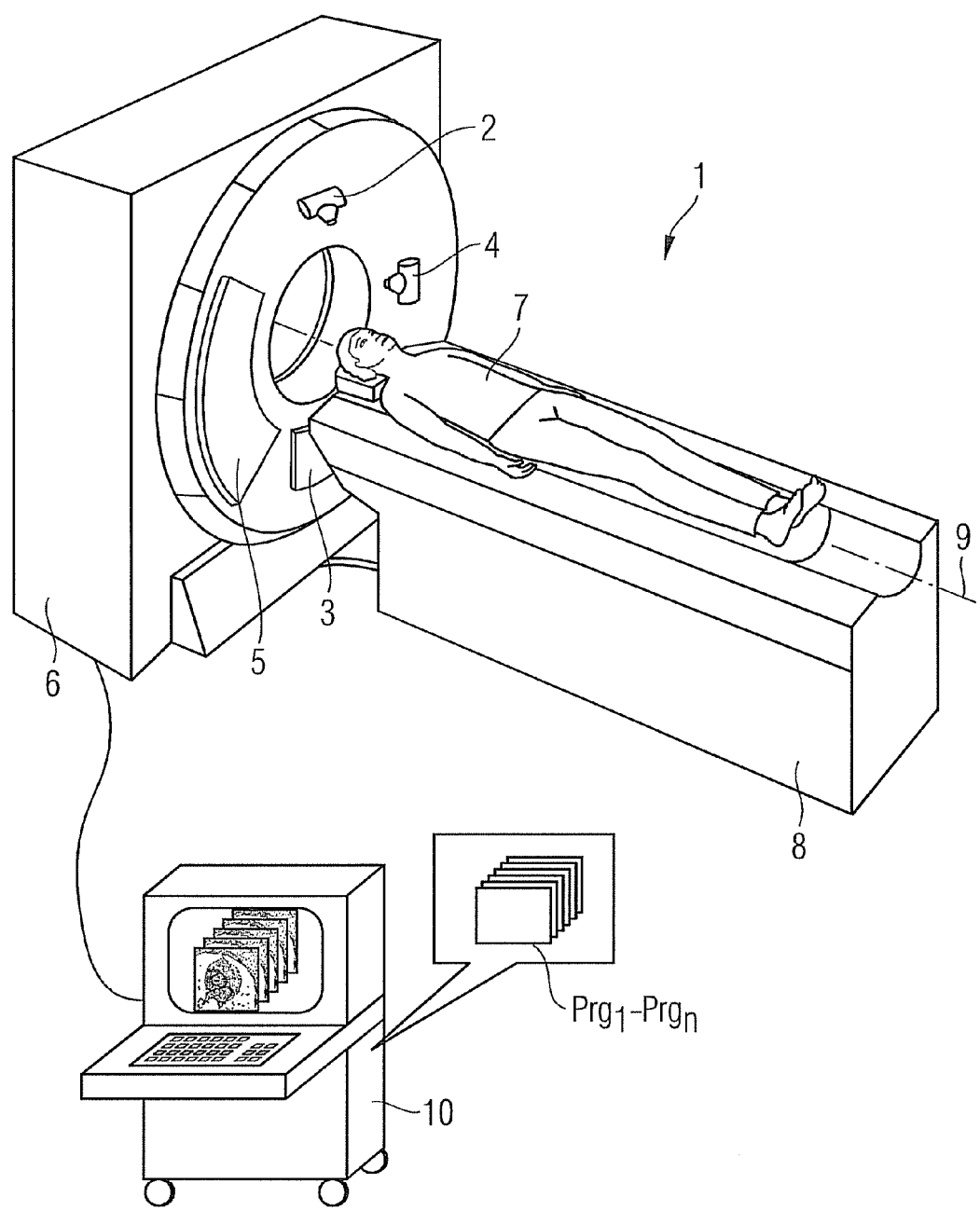
FIG. 3: is a CT system with a quantum-counting detector for carrying out an embodiment of the inventive method.

An embodiment of the inventive method can be used in combination with any detectors with counting detector elements. Purely by way of example, a computed tomography system 1 with detectors configured according to the invention is shown in FIG. 3. This CT system 1 has a gantry housing 6, in which a gantry with a radiation source 2 is arranged which rotates together with an opposing detector 3 about a system axis 9. Optionally, at least one second radiation source 4 and one opposing detector 5 can be arranged on the gantry. For scanning, for example, a patient 7 is moved on a patient support 8 through the measurement field, while the radiation sources 2, 4 and the detectors 3, 5 rotate on the gantry about the system axis 9.

The signals detected by the detector 3 and/or 5 can be processed directly in a detector electronic system configured or adjusted according to an embodiment of the invention or in a suitably configured or programmed central computer station 10. Computer programs Prg1-Prgn which, in operation, carry out inter alia an embodiment of the inventive method, can also be stored therein.

It is noted that embodiments of the inventive method and embodiments of the inventive circuit arrangement are not restricted to tomographic applications, but are usable with any particle detecting or photon detecting detector with counting detector elements.

Summarizing, therefore, with embodiments of the invention, a method, a circuit arrangement and an X-ray system, in particular a CT-system are proposed in which, in order to correct the count rate drift of a detector for ionizing radiation with quantum-counting detector elements which comprise a combination of at least two counters with significantly different energy thresholds, and based on previously determined functional dependencies of count rates on one another and using at least one of the counters per detector element as a reference, the count rates of the respective other counters with a different energy threshold are corrected.

Although the invention has been illustrated and described in greater detail by means of the preferred exemplary embodiment, the invention is not restricted by the examples disclosed and other variations may be derived by a person skilled in the art, without departing from the protective scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent-claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for correcting count rate drift in a detector for ionizing radiation including a plurality of quantum-counting detector elements arranged over an area, each detector element including a combination of at least two counters with different energy thresholds which are evaluated in combination in order to determine an incident radiation dose, the method comprising:
    correcting, based on count rate drift ratios of the at least two counters, the count rates of the at least two counters, the count rate drift ratios being calculated using at least one of the at least two counters as a reference.

2. The method of claim 1, wherein the count rate drift ratios of the individual counters of each detector element are measured under irradiation of the identical or, with regard to the absorption properties thereof, equivalent material of different thickness which will also be present, at least approximately, in a later X-ray investigation in a measurement object that is to be investigated.

3. The method of claim 2, wherein at least one of the measured count rates and a logarithmic equivalent thereof are subjected, before use thereof, to normalization.

4. The method of claim 3, wherein a flat field correction is used for normalization.

5. The method of claim 2, wherein, in order to determine the count rate drift ratios, coefficients of a linear regression are determined between the at least two counters.

6. The method of claim 1, wherein, in order to determine the count rate drift ratios of the detector elements of the detector, coefficients of a linear regression are determined between the at least two counters.

7. The method of claim 1, wherein said method is used for an X-ray detector.

8. The method of claim 1, wherein said method is used for a CT detector.

9. The method of claim 1, wherein, in order to determine the count rate drift ratios, coefficients of a polynomial regression are determined between the at least two counters.

10. A non-transitory computer readable medium including program segments for, when executed on a computer device, causing the computer device to implement the method of claim 1.

11. A method for correcting count rate drift in a detector for ionizing radiation including a plurality of quantum-counting detector elements arranged over an area, each detector element including a combination of at least two counters with different energy thresholds which are evaluated in combination in order to determine an incident radiation dose, the method comprising:
    correcting, based on previously determined functional dependencies of count rates on one another and using at least one of the at least two counters per detector element as a reference, the count rates of the respective other counters with a different energy threshold, wherein, in order to determine the functional dependencies of the count rate drift of the detector elements of the detector, coefficients of a polynomial regression are determined between the at least two counters and thus the count rate of at least one counter of the at least two counters is corrected.

12. A non-transitory computer readable medium including program segments for, when executed on a computer device, causing the computer device to implement the method of claim 11.

13. An X-ray system, comprising:
    a detector with quantum-counting detector elements, a combination of at least two counters with different energy thresholds being associated with each of the detector elements; and
    a control and computer unit including a program memory in which computer programs are stored and which, during operation, corrects, based on count rate drift ratios of the at least two counters, the count rates of the at least two counters, the count rate drift ratios being calculated using at least one of the at least two counters as a reference.

14. The X-ray system of claim 13, wherein the X-ray system is a CT system.

15. A circuit arrangement for quantum-counting detector elements, a combination of at least two counters with different energy thresholds being associated with each of the detector elements, the circuit arrangement being configured to, during operation, correct, based on count rate drift ratios of the at least two counter, the count rates of the at least two counters, the count rate drift ratios being calculated using at least one of the at least two counters as a reference.

* * * * *